(12) United States Patent
Van-Dinh et al.

(10) Patent No.: US 11,839,633 B2
(45) Date of Patent: Dec. 12, 2023

(54) COMPOSITION AND METHOD OF TREATING GASTROINTESTINAL DISEASE WITH MICROBIAL AND SOY MIXTURE

(71) Applicant: SVK Herbal Corporation, Ho Chi Minh (VN)

(72) Inventors: Cuong Van-Dinh, San Jose, CA (US); Nam Van Tran, Ho Chi Minh (VN); Phuong Chien Le, Ho Chi Minh (VN); Hai Hoang Nguyen, Ho Chi Minh (VN)

(73) Assignee: SVK Herbal Corporation, Ho Chi Minh (VN)

( * ) Notice: Subject to any disclaimer, the term of this patent is extended or adjusted under 35 U.S.C. 154(b) by 521 days.

(21) Appl. No.: 16/821,808

(22) Filed: Mar. 17, 2020

(65) Prior Publication Data

US 2021/0290695 A1    Sep. 23, 2021

(51) Int. Cl.

| | |
|---|---|
| *A61K 35/744* | (2015.01) |
| *A61K 35/742* | (2015.01) |
| *A61K 36/06* | (2006.01) |
| *A61K 36/48* | (2006.01) |
| *A61K 36/9066* | (2006.01) |
| *A61K 36/54* | (2006.01) |
| *A61K 9/08* | (2006.01) |
| *A61K 9/14* | (2006.01) |
| *A61K 9/48* | (2006.01) |
| *A61K 9/00* | (2006.01) |
| *A61P 1/04* | (2006.01) |
| *A61P 1/08* | (2006.01) |
| *A61P 1/12* | (2006.01) |
| *A61K 9/20* | (2006.01) |

(52) U.S. Cl.
CPC .......... *A61K 35/744* (2013.01); *A61K 9/0053* (2013.01); *A61K 9/08* (2013.01); *A61K 9/14* (2013.01); *A61K 9/20* (2013.01); *A61K 9/4808* (2013.01); *A61K 35/742* (2013.01); *A61K 36/06* (2013.01); *A61K 36/48* (2013.01); *A61K 36/54* (2013.01); *A61K 36/9066* (2013.01); *A61P 1/04* (2018.01); *A61P 1/08* (2018.01); *A61P 1/12* (2018.01)

(58) Field of Classification Search
None
See application file for complete search history.

(56) References Cited

U.S. PATENT DOCUMENTS

| | | | |
|---|---|---|---|
| 2002/0037341 A1* | 3/2002 | Heo et al. ............ | C07K 16/121 426/34 |
| 2002/0182274 A1* | 12/2002 | Lu et al. ................. | A61P 9/04 424/757 |
| 2009/0175911 A1* | 7/2009 | Cutting et al. ........ | A23L 33/135 424/93.46 |
| 2011/0136745 A1* | 6/2011 | Bringe et al. ........... | A61P 29/00 426/594 |
| 2017/0020161 A1* | 1/2017 | Kim, II et al. ........ | A23K 10/14 |

FOREIGN PATENT DOCUMENTS

| | | | |
|---|---|---|---|
| CN | 103417583 A | * | 12/2013 |
| JP | 200133504 A | * | 12/2001 |
| JP | 2019064997 A | * | 4/2019 |
| KR | 2004062000 A | * | 7/2004 |

OTHER PUBLICATIONS

Chen et al., "Probiotics and Prebiotics: Role in Clinical Disease States", Advances in Pediatrics, Chapter 5, vol. 52, pp. 77-113 (Year: 2015).*

Kwiecien et al., "Curcumin: A Potent Protectant against Esophageal and Gastric Disorders", International Journal of Molecular Sciences, vol. 20, pp. 1-14 (Year: 2019).*

Checinska et al., "Bacillus and Other Spore-Forming Genera: Variations in Responses and Mechanisms for Survival", Annual Review of Food Science and Technology, vol. 6, pp. 351-369 (Year: 2015).*

Gomez et al., "Avocado Seeds: Extraction Optimization and Possible Use as Antioxidant in Food", Antioxidants, vol. 3, pp. 439-454 (Year: 2014).*

* cited by examiner

*Primary Examiner* — Michelle F. Paguio Frising

(74) *Attorney, Agent, or Firm* — David R. Stevens; Stevens Law Group

(57) ABSTRACT

The composition is an herbal supplement comprised of hydrolyzed whole soybean, *Bacillus amyloliquefaciens*, lactic acid bacteria, the mushroom, *Auricularia polytricha*, and turmeric. The soybean feeds the bacterial components of the composition to increase their biomass. The *Bacillus amyloliquefaciens* produces protease and amylase enzymes which hydrolyze the proteins and carbohydrates in the soybean into smaller peptides and oligosaccharides. These smaller nutrients are more easily absorbed by the gastrointestinal tract. The lactic acid bacteria are probiotics which limit the growth of *Bacillus amyloliquefaciens* in the composition thus balancing the gastrointestinal microbiome. The mushroom, *Auricularia polytricha* enhances blood flow, removes toxins from the bowel, stabilizes the digestive system and enhances digestion. Turmeric is an antioxidant, anti-ulcer, anti-bacteria (including the suppression of *Helicobacter pylori* bacteria), anti-inflammatory. Methods of using the composition include treatment and prevention of disease of the gastrointestinal tract, the cardiovascular system, and lowering cholesterol.

20 Claims, 5 Drawing Sheets

```
┌─────────────────────────────────────┐
│ In sterile tube, culture B.a. in a  │
│        Microbial Culture Medium     │
│                 100                 │
└─────────────────────────────────────┘
                  │
                  ▼
┌─────────────────────────────────────┐
│ Transfer to a 500 ml container      │
│ containing 100 ml of Microbial      │
│         Culture Medium              │
│                 110                 │
└─────────────────────────────────────┘
                  │
                  ▼
┌─────────────────────────────────────┐
│ Biomass Production at Room          │
│         Temperature (3 days)        │
│                 120                 │
└─────────────────────────────────────┘
                  │
                  ▼
┌─────────────────────────────────────┐
│ Transfer 10% by volume of Culture   │
│ to a 500 ml Container containing    │
│   250 ml of Microbial Culture Medium│
│                 130                 │
└─────────────────────────────────────┘
                  │
                  ▼
┌─────────────────────────────────────┐
│ Biomass Production at Room          │
│         Temperature (3 days)        │
│                 140                 │
└─────────────────────────────────────┘
                  │
                  ▼
┌─────────────────────────────────────┐
│     Sterile B.a. Biomass Solution   │
│                 150                 │
└─────────────────────────────────────┘
```

Figure 1

COMPOSITION AND METHOD OF TREATING GASTROINTESTINAL DISEASE WITH MICROBIAL AND SOY MIXTURE

BACKGROUND

Field of the Invention

This disclosure relates to compositions and methods of prevention or treatment of illness using a soy-based product.

Background of the Invention

Patients suffering from disease, particularly diseases of the gastrointestinal tract often suffer from malnutrition. This may be in part due to a reduced ability to digest and absorb nutrients. When nutrients such as proteins and polysaccharides are provided in simpler form (peptide and simpler sugars), they are easier to absorb.

Typically, nutritional supplements do not have medicinal properties. In contrast, compounds and compositions that possess medicinal properties typically do not provide nutritional support.

A composition is needed which supports the nutritional needs of a patient in an easy to digest and absorb manner as well as provides treatment or prophylaxis of disease.

BRIEF SUMMARY OF THE INVENTION

We disclose a composition and method of using the composition to treat or prevent gastrointestinal disease. The composition may comprise a plant-based material which may include soybean, seeds, fruit, or combinations thereof. The composition may further include *Bacillus amyloliquefaciens*, a plurality of strains of lactic acid bacteria, *Auricularia polytricha*, and *Curcuma longa* (turmeric). In embodiments in which the plant-based material includes fruit, the fruit may be avocado. In embodiments in which the plant-based material includes soybeans, the soybeans may be whole soybeans. In some embodiments in which the plant-based material includes soybeans, the soybeans may be fermented.

The *Bacillus amyloliquefaciens* may be provided as endospores, vegetative cells, or a combination of endospores and vegetative cells. In some embodiments, the *Bacillus amyloliquefaciens* may ferment the soybeans, seeds, fruit, or combinations thereof.

In some embodiments, the plurality of strains of lactic bacteria may include at least one of the following: *Lactobacillus bulgaricus, Streptococcus thermophilus,* and *Lactobacillus casei*. In some embodiments, the plurality of lactic bacterial may include each of *Lactobacillus bulgaricus, Streptococcus thermophilus,* and *Lactobacillus casei*. In some embodiments, the plurality of strains of lactic bacterial may be *Lactobacillus bulgaricus, Streptococcus thermophilus,* and *Lactobacillus casei*.

The disclosed composition may be used to treat or prevent a variety of gastrointestinal diseases. These gastrointestinal diseases may include one or more of the following list: gastrointestinal tumors, gastrointestinal infection, constipation, malnutrition, indigestion, nausea, diarrhea, abdominal pain, flatulence, irritable bowel syndrome, chronic hepatitis, gastritis, gastrointestinal ulcer, gastrointestinal inflammation, gastric *Helicobacter pylori* infection, GERD (gastroesophageal reflux disease), hemorrhoids, and polyps of the colon or rectum.

In some embodiments, the composition may be provided to a human. In other embodiments, the composition may be provided to a non-human animal. In some embodiments, the composition may be provided to a mammal.

In some embodiments, the composition may be provided as any one or more of a solution, a dried powder, a tablet, or a capsule.

The composition may be administered orally and provided according to a variety of dosing schedules. In some embodiments, the composition may be administered orally at least once per day. In some embodiments, the composition may be administered orally three times per day. In some embodiments, the composition may be administered orally before a meal. In some embodiments, the composition may be administered orally three times per day, each time before a meal.

The composition as disclosed herein may be administered to a subject in need as a solution in a variety of volumes. In some embodiments, the solution may be administered in a volume of between 50 ml and 300 ml. In some embodiments, the composition may be administered at least once per day in a volume of between 50 ml and 300 ml per dose. In some embodiments, the composition may be administered three times per day in a volume between 50 ml and 100 ml per dose.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings.

FIG. 1 illustrates an embodiment of a method of producing a *Bacillus amyloliquefaciens* solution for use in preparing the disclosed composition.

DETAILED DESCRIPTION OF THE INVENTION

Definitions

Figure 2:
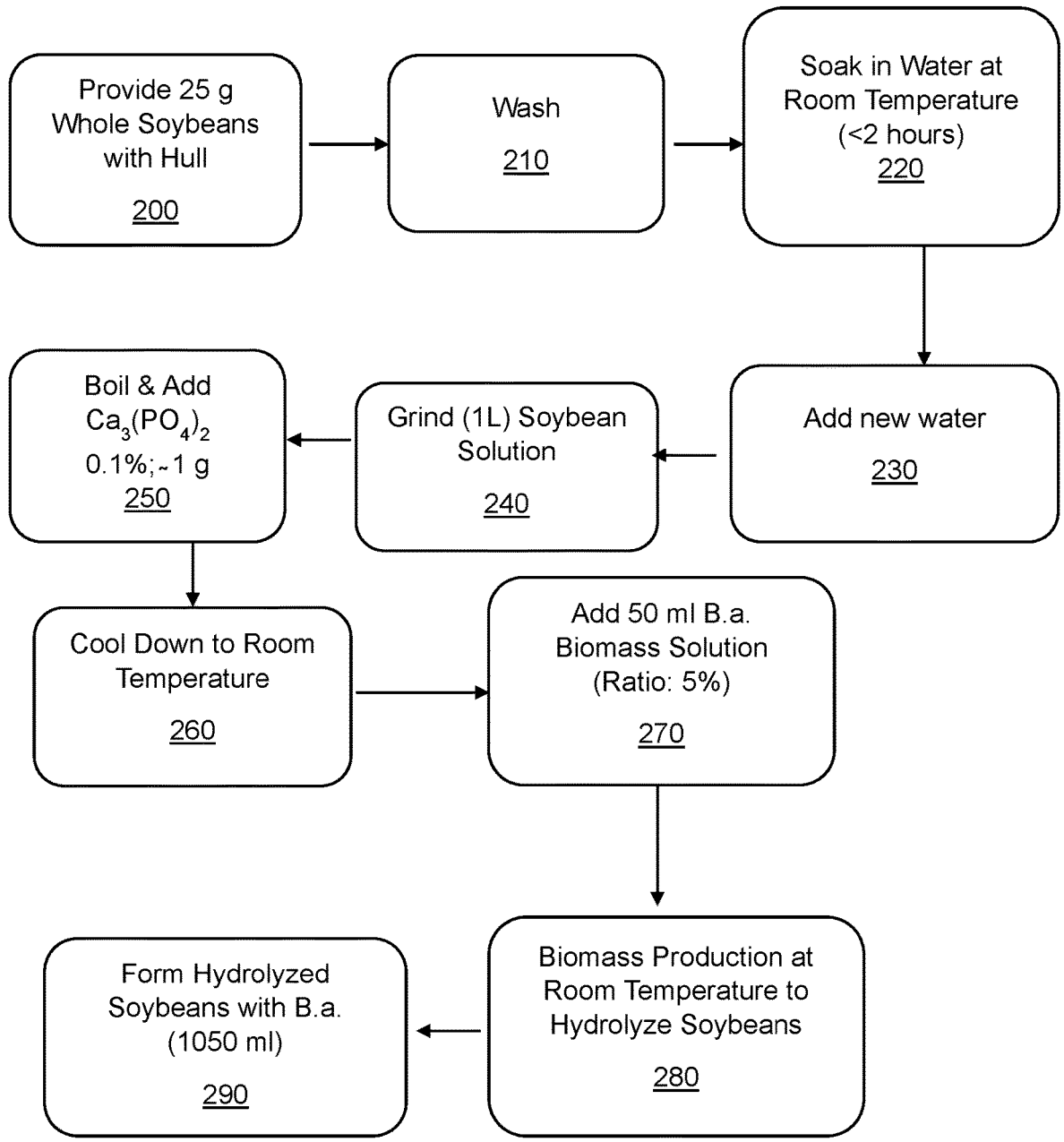
FIG. 2 illustrates an embodiment of a method of producing a hydrolyzed soybean solution with increased *Bacillus amyloliquefaciens* biomass.

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a composition, methods of using the composition for treatment and prophylaxis of disease, and methods of producing the composition. The composition is produced from soluble and insoluble fibers derived from a plant source, antiplatelet compounds, and amino acids of plant origin. The composition may improve the functioning of the digestive system: complete the task of digestion of carbohydrate, lipid, protein substances; balance harmful and beneficial bacteria; strengthen the activity of the immune system and prevent bacterial and viral infections. Furthermore, the composition may enhance blood circulation, bring nutrients and oxygen to the arteries to nourish the organs including the liver, kidneys, pancreas, spleen; help the organs to better perform the task of digestion and enhance the process of detoxification of the body (aids in the metabolism process, supports in the treatment of atherosclerosis, diabetes, overweight, etc.), The composition is also a supply of nutrients to the body including, but not limited to amino acids, vitamins, and trace elements.

The disclosed composition may be produced from whole soybeans, including the protective outer seed coat. When the whole soybeans are added to the composition in a very pureed form, all soluble fibers and celluloses of the soybeans may be retained, and the nutrients provided by the soybeans may be easily absorbed into the body. At the same time this method of production adheres to no-waste, eco-friendly production goals.

The soybeans in the composition may be hydrolyzed by enzymes generated from *Bacillus amyloliquefaciens* and then preserved by the lactic acids generated from one or more of *Lactobacillus bulgaricus, Streptococcus thermophilus*, and *Lactobacillus casei* bacteria.

In some embodiments, soybean may be substituted with seeds or fruit, for example, avocado.

The disclosed composition provides the body with nutrients from the main components of soybean, as proteins and carbohydrates are hydrolyzed into substances with smaller and simpler molecular weights and structures. This allows ease of absorption into the body as oligopeptides, peptides, oligosaccharides and saccharides are converted from proteins and carbohydrates, respectively, and thus requires less energy for their digestion.

In addition to being useful for nutritional purposes, the oligosaccharides from soybeans and fermented soybeans may help prevent gastrointestinal infections as well as tumor activities. They may boost the level of resistance of the intestine to these pathologies, possibly by modifying the intestinal immune responses.

The additional ingredients in the disclosed composition are discussed below.

*Bacillus amyloliquefaciens*

Soybean is used as a nutrient medium to feed, and thereby increase, the biomass of the *Bacillus amyloliquefaciens*, and lactic bacteria. At the same time, *Bacillus amyloliquefaciens* secretes protease and amylase enzymes which digest the protein and carbohydrate of the soybeans into smaller molecules. Consequently, the nutrients in soybeans become easier to absorb into the body. At the same time, these enzymes may aid the digestive process of the intestinal tract, assisting in the digestion of other foods the user has consumed. In some embodiments, the *Bacillus amyloliquefaciens* bacteria may be isolated from the traditional fermented soybean paste "CHAO" of Vietnam.

*Bacillus amyloliquefaciens* have the capability to produce endospores. In some embodiments, the *Bacillus amyloliquefaciens* is added as a combination of endospores and vegetative cells. In some embodiments, the *Bacillus amyloliquefaciens* is added as a combination of spores and vegetative cells.

*Bacillus amyloliquefaciens* thrives at the neutral pH level (pH 6.5-7.5) found in the small intestine. Its spores and living cells continue to survive and divide in the intestinal tract under typical intestinal conditions. Consequently, once they reach the intestinal tract, *Bacillus amyloliquefaciens* bacteria continue to create new bacterial cells, which further support good digestion.

Once in the intestine, *Bacillus amyloliquefaciens* may continue to provide the benefits they add to the composition. The protease and amylase enzymes continue to digest nutrients and the spores, which can easily cope with a fluctuated environment including changes in temperature, pH, etc., create new bacterial cells under favorable conditions. These cells may continue to live and work, producing more protease and amylase enzymes.

In addition to improving nutrient digestion, *Bacillus amyloliquefaciens* bacteria may reduce the formation of platelets (thereby reducing thrombosis) in the blood vessels and improve blood circulation.

*Lactobacillus bulgaricus, Streptococcus thermophilus*, and *Lactobacillus casei*

One or more of the probiotics, *Lactobacillus bulgaricus, Streptococcus thermophilus*, and *Lactobacillus casei*, may be included in the composition. The probiotics prevent bacterial contamination from outside the body while limiting the growth of *Bacillus amyloliquefaciens* bacteria. The latter function prevents the soybean material from becoming over fermented which may increase the biomass of the *bacillus* strains and result in a pungent odor. Furthermore, upon entering the digestive system, the lactic bacteria help stabilize the gastrointestinal microbiota, thus inhibit the growth of harmful bacteria.

Presence of lactic bacteria in the intestinal tract also has a positive effect of balancing the microbial system in the digestion system, thus inhibiting the growth of harmful bacteria.

*Auricularia polytricha*

When ground extensively and added to the other components in the composition, *Auricularia polytricha* mushroom emulsifies the other components and creates a uniform product. Its ability to act as an emulsifier may enable it to cleanse the body of liquid toxins.

When present in the intestinal tract, *Auricularia polytricha* may assist in the prevention of constipation, at least in part by increasing food movement through the intestinal tract. It may cause detoxification in the body, especially in the colon and rectum.

*Auricularia polytricha* may lower fats, including cholesterol, in blood and internal organs and enhance blood circulation. It may cleanse the walls of arteries and veins, thereby preventing the formation of plaques, platelets, blood clots. *Auricularia polytricha* may help digest food and provide nutrients itself. Results attained from numerous studies report that it contains low levels of cholesterol and calories but protein and vitamin B content. It contains micronutrients, copper, iron, magnesium, selenium, zinc. *Auricularia polytricha* also provides soluble fibers, omega fatty acids, e.g., linoleic acid and antioxidants. Finally, *Auricularia polytricha* may cause loss of appetite, thus reducing body weight.

Curcumin

Curcumin is a key substance in turmeric. Curcumin may have the following therapeutic or prophylactic properties: protection of liver cells, anti-dyslipidemia, anti-inflammatory properties, anti-bacterial properties, the ability to heal ulcers, antioxidant properties, and the ability to induce apoptosis (programmed cell death).

The components of the disclosed composition work together to achieve the physiological responses discussed herein. For example, there is a synergistic relationship between *Bacillus amyloliquefaciens* and *Auricularia polytricha*. *Bacillus amyloliquefaciens* provides bio-chemical effects, create enzymes able to resolve nutrients including protein, carbohydrates, and cholesterol while *Auricularia polytricha* boosts the mechanical peristaltic effects in the intestine and the arteries. The viscous properties of *Auricularia polytricha* enable it to absorb the toxins lining the mucosa and discharge them from the body.

Uses of the Disclosed Composition

The composition's uses include to (1) stabilize the digestion system, (2) detoxify the body and clean the mucous membranes, (3) lower the cholesterol level in blood and internal organs, (4) boost the immune system, and (5) improve blood circulation Stabilize the Digestive System Protease and amylase enzymes secreted from the two *bacillus* strains may stimulate actions of the digestive system. The three lactic bacteria may create a low pH environment (approximate pH level<5.5) which may help reduce harmful bacteria in the intestine. The mixture of the probiotics (in some embodiments, a *bacillus* strain and three lactic bacteria) and *Auricularia polytricha* may stabilizes the digestive system and enhance digestion.

Detoxify the Body and Clean the Mucous Membranes

The viscous property of *Auricularia polytricha* may cleanse the surface of the mucous membranes and cause residues to be excreted at a faster rate. It may also help in the cleansing of liquid toxins from the body through sweat and urination. Furthermore, *Auricularia polytricha* may help disintegrate various stones formed by the bonding of multiple mineral residues in the body.

Lower Cholesterol in Blood and Internal Organs and Enhance Blood Circulation

*Auricularia polytricha* may reduce the formation of plaques in the arteries and veins, at least in part, by reducing serum cholesterol which may be part of the plaque. The *Bacillus amyloliquefaciens* bacteria reduce the formation of platelets and thereby, reduce thrombosis, and enhance blood circulation. Clots are also part of plaques. Combined, these components prevent and treat plaques, strokes and improve blood circulation.

In summary, the disclosed composition is a combination of nutrients from soybean, probiotics (*Bacillus amyloliquefaciens*) and herbal ingredients (*Auricularia polytricha*) which, when combined, have synergistic effects. The concurrent improvements in blood circulation, digestive system, and detoxification ability of the body boost the immune system and makes this mixture unique. The deterioration of these systems is the etiology of chronic diseases. A remedy of chronic diseases is most effective when these deteriorations can be treated concurrently.

As a conduit to bring active substances to the affected areas, the disclosed composition may be combined with other therapeutics, for example, pharmaceutical products, to provide specialized treatments. It is also a good source of nutrients, which is especially beneficial for sick patients who have difficulty absorbing nutrients in foods. The disclosed composition is unique with its dual uses, serving as a source of nutrients while possessing medicinal properties to treat or prevent disease.

The composition may be delivered orally according to a variety of dosing schedules. It may be ingested at a number of doses which may vary depending on the severity of the illness. For example, the composition may be ingested once, twice, three times, or four times per day. The dosing may continue for a length of time which may depend of the severity of the illness or continued indefinitely to prevent future illness. For example, the dosing may continue for one day, one week, one month, six months, one year, or any length of time in between these examples.

In some embodiments, the composition may be provided in a liquid form. When provided in liquid solution as described herein, each dose of the composition may include 10 ml, 50 ml, 100 ml, 150 ml, 200 ml, or 300 ml. In some embodiments, the composition may be provided in a liquid volume of between 50-100 ml, between 50-300 ml, or between 150-200 ml.

In other embodiments, the composition may be provided in a lyophilized (dried) powder. In other embodiments, the composition may be dried and either pressed into a tablet or provided in a capsule.

Figure 5:
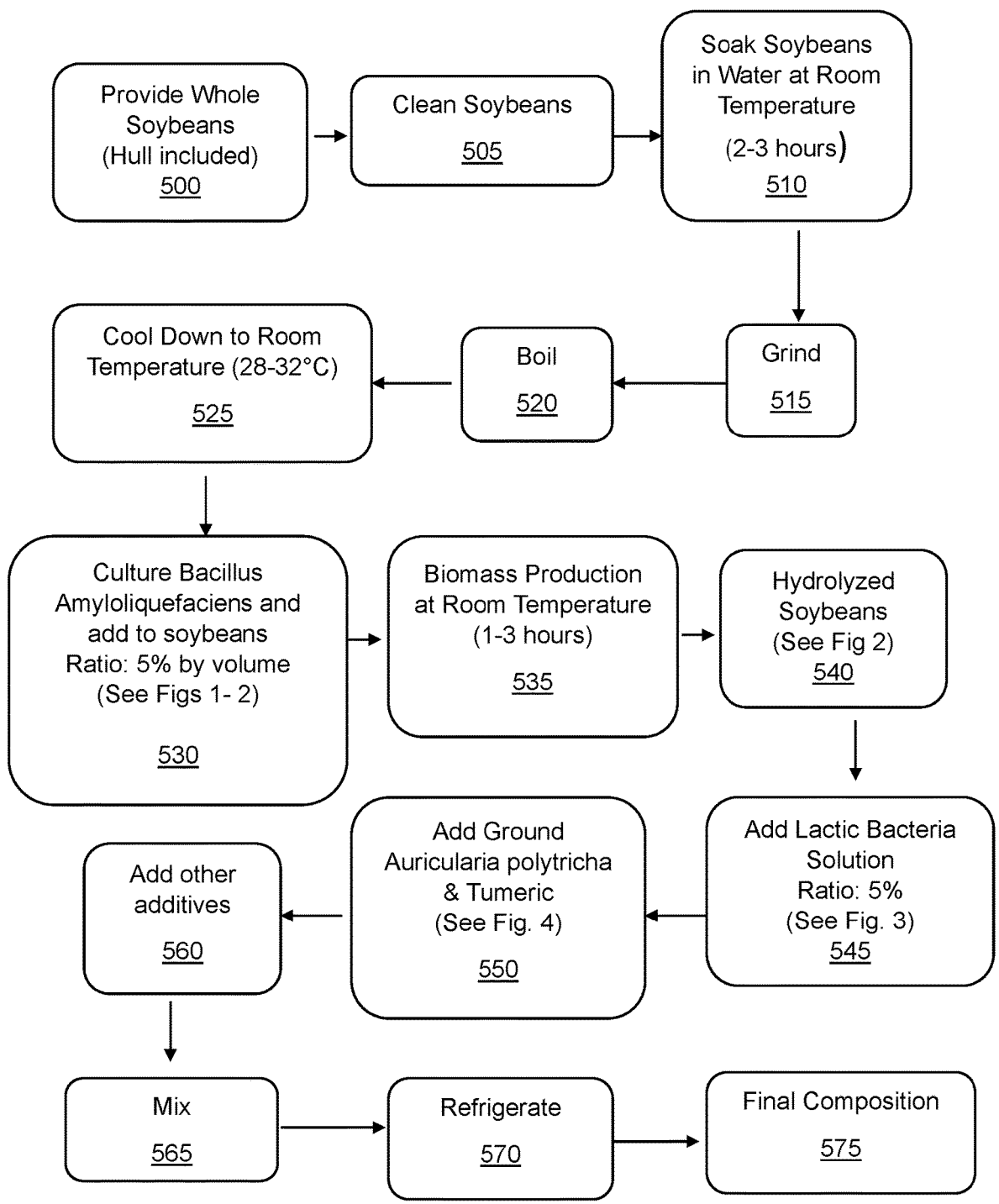
FIG. 5 illustrates an embodiment of a method of producing the disclosed composition including the solutions illustrated in FIGS. 1-4.

Referring now to the drawings, FIG. 1 illustrates a flow chart which discloses an embodiment of a method of producing a *Bacillus amyloliquefaciens* solution (B.a.) which may be used to produce the disclosed composition. In step 100, a sterile tube containing an appropriate microbial culture medium as known in the art is inoculated with *Bacillus amyloliquefaciens*. The *Bacillus amyloliquefaciens* cells are allowed to divide. Then the microbial culture medium comprising *Bacillus amyloliquefaciens* is transferred to a 500 ml container containing 100 ml of bacterial culture medium (step 110). The culture is allowed to divide at room temperature for 3 days (step 120) to increase the biomass of the *Bacillus amyloliquefaciens*. In step 130, 10% (+/−1%) by volume of the contents of the 500 ml container is transferred to a second 500 ml container which contains 250 ml of microbial culture medium. The culture is allowed to divide (biomass production) for 3 days (step 140). The final product comprises the *Bacillus amyloliquefaciens* biomass solution (step 150) used in the disclosed composition as illustrated in FIG. 5.

FIG. 2 illustrates a flow chart which discloses an embodiment of a method of producing a *Bacillus amyloliquefaciens* and hydrolyzed soybean solution which may be used to produce the disclosed composition. In step 200, 25 g of whole soybeans including the hulls are provided. The whole soybeans are then washed (step 210) and then soaked in water at room temperature for less than 2 hours (step 220). Additional water is added (step 230) and 1 L of the soybeans in water are ground (step 240). The ground soybeans are boiled and Ca3(PO4)2 is added (approximately 1 g) to result in a 0.1% Ca3(PO4)2 solution (step 250). In step 260, the boiled solution is cooled to room temperature. Approximately 50 ml of the *Bacillus amyloliquefaciens* biomass solution as produced according to FIG. 1 is added at a volume of approximately 5% of the soybean solution (step 270). The combined *Bacillus amyloliquefaciens* biomass solution and soybean solution are incubated at room temperature (step 280) to increase the biomass of the *Bacillus amyloliquefaciens* and hydrolyze the soybeans. The resulting product comprises hydrolyzed soybeans and increase *Bacillus amyloliquefaciens* biomass (step 290).

Figure 3:
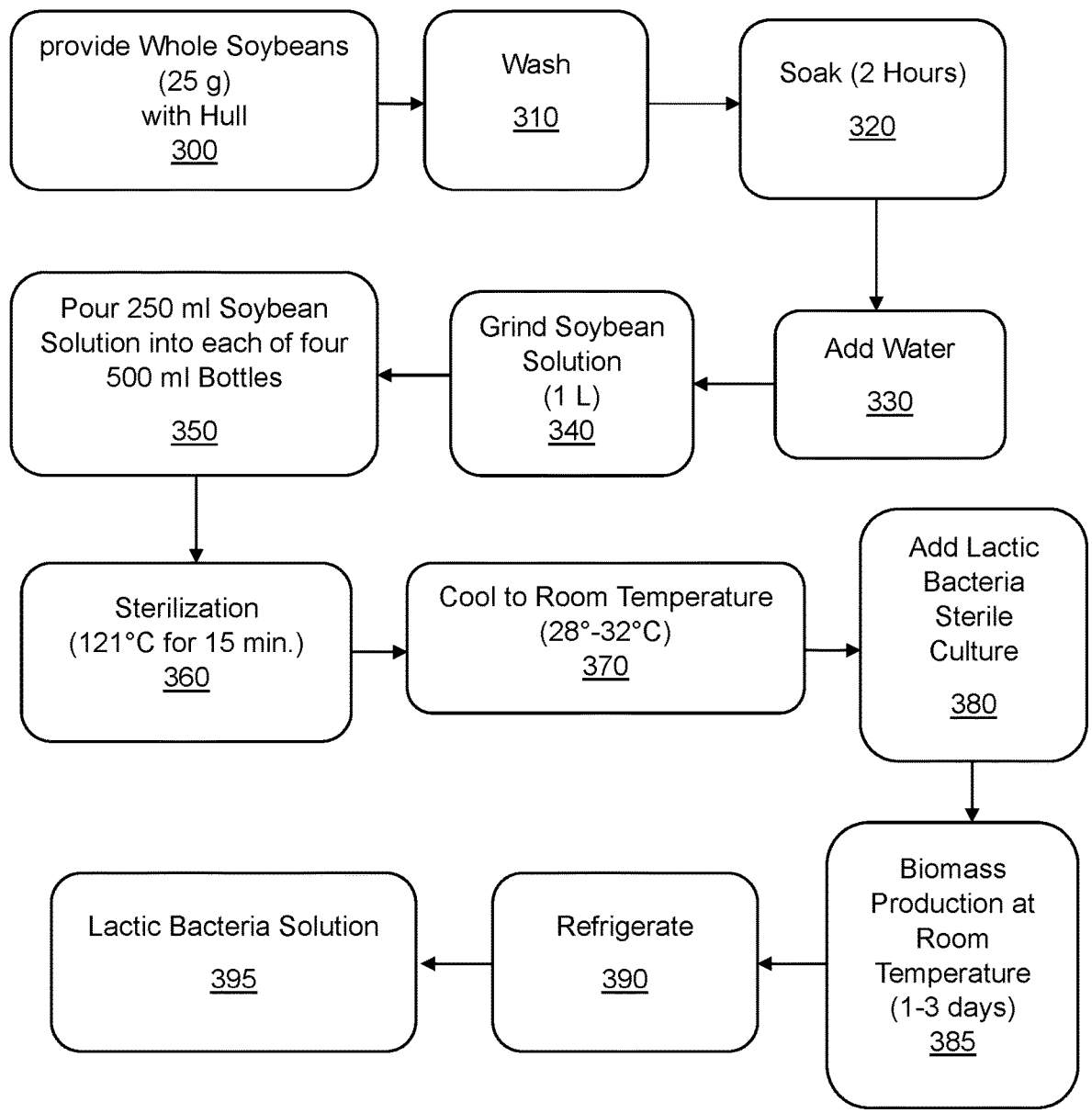
FIG. 3 illustrates an embodiment of a method of producing a lactic bacteria solution for use in preparing the disclosed composition.

FIG. 3 illustrates a flow chart which discloses an embodiment of a method of producing a lactic bacterial solution which may be used to produce the disclosed composition. In step 300, 25 g of whole soybeans including the hull are provided. The soybeans are washed in step 310. The soybeans are then soaked for 2 hours (step 320). Water is added to a final volume of 1 L (step 330). The soybean solution is then ground (step 340). The ground soybean solution is divided equally into four 500 ml bottles. Consequently, 250 ml of the ground soybean solution is added to each 500 ml bottle (step 350). The ground soybean solution is sterilized at 121° C. for 15 minutes (step 360). The sterilized solution is allowed to cool to room temperature (28-32° C.) (step 370). The cooled solution is inoculated with lactic bacteria culture (step 380). The lactic bacteria culture is allowed to incubate at room temperature for 1-3 days thereby producing an increased biomass (step 385). The biomass solution is then refrigerated (approximately 4° C.) (step 390). The final product comprises the lactic bacteria solution (step 395) used in the disclosed composition as illustrated in FIG. 5.

Figure 4:
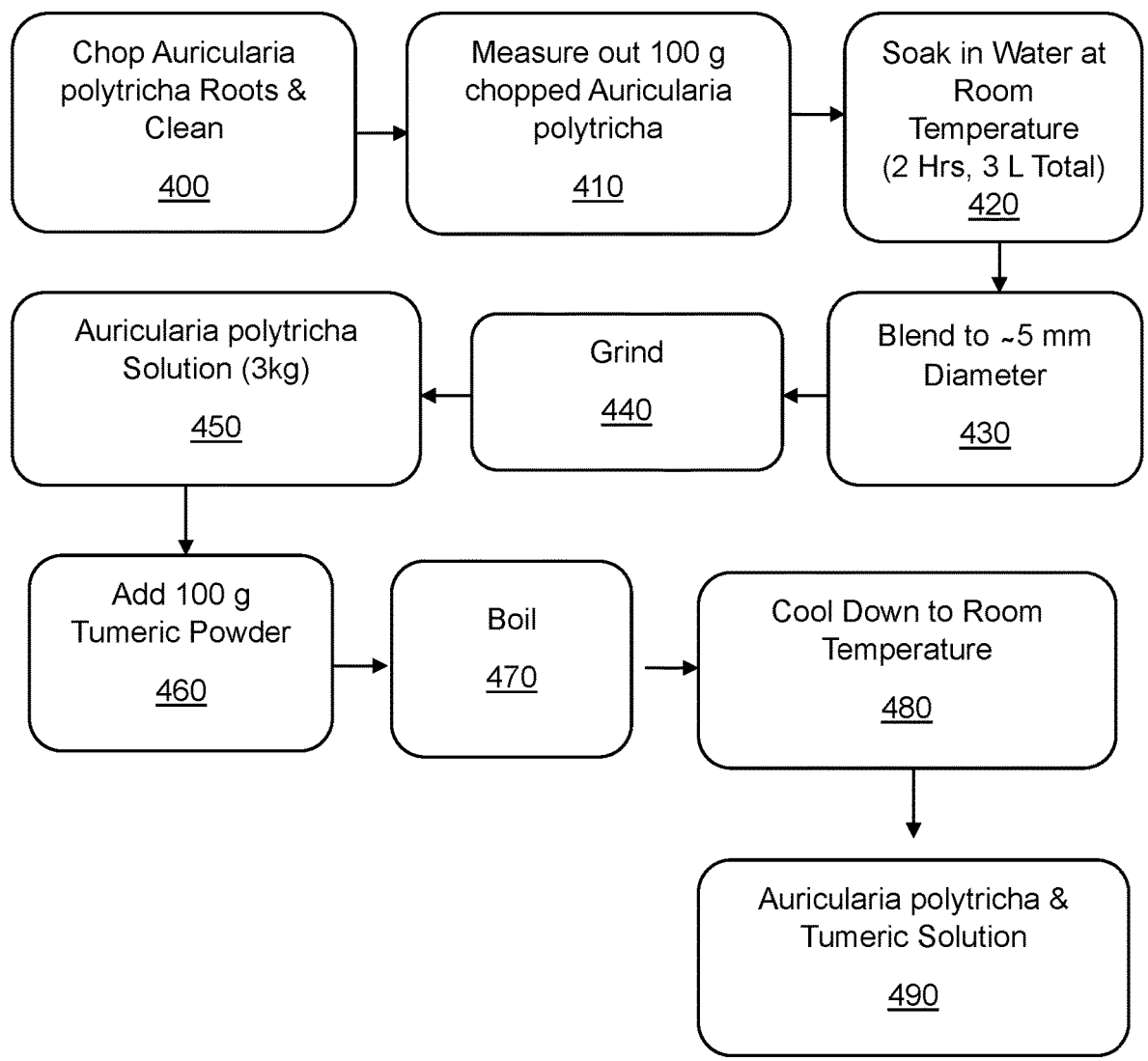
FIG. 4 illustrates an embodiment of a method of producing an *Auricularia polytricha* and curcumin solution for use in preparing the disclosed composition.

FIG. 4 illustrates a flow chart which discloses an embodiment of a method of producing a solution of *Auricularia polytricha* and curcumin. In step 400, *Auricularia polytricha* roots are chopped and cleaned. Approximately 100 g of the chopped *Auricularia polytricha* roots are measured out (step 410) and soaked in room temperature water for 2 hours in a total volume (roots and water combined) of 3 L (step 420). In step 430, the soaked roots are blended to produce fragments with a diameter of approximately 5 mm (+/−2 mm). In step 440, the blended roots are ground. The ground roots in water result in a 3 kg solution (step 450). In step 460, 3 g of curcumin powder is added. The solution is then boiled (step 470) and cooled to room temperature (step 480). The resulting product comprises the *Auricularia polytricha* and curcumin solution used in the disclosed composition as illustrated in FIG. 5.

FIG. 5 illustrates a flow chart which discloses an embodiment of a method of producing the disclosed composition using the materials as disclosed in FIGS. 1-4. In step 500, whole soybeans including the hulls are provided. The soybeans are then cleaned (step 505). In step 510, the soybeans are soaked in water at room temperature for 2-3 hours. Next, the soaked soybeans are ground (step 515) and then boiled (step 520). The ground and boiled soybeans are then allowed to cool down to room temperature (28°-32° C.) (step 525). In step 530, culture *Bacillus amyloliquefaciens* as shown in FIGS. 1 and 2 and add to the soybeans in a volume of 5% of the total volume of the soybeans (e.g. 50 ml *Bacillus amyloliquefaciens* to 1 L soybeans). Allow biomass production at room temperature for 1-3 hours (Step 535). The soybeans will hydrolyze during biomass production (step 540). In Step 545, add lactic bacterial solution (see FIG. 3) at a ratio of 5% (+/−1%) of the total volume of soybeans. Then add the ground *Auricularia polytricha* and turmeric solution as described in FIG. 4 (step 550). Add other additives which may include, but are not limited to, natural essences, colors, and sweeteners, for example, *stevia* (step 560). Mix the added ingredients (step 565) and refrigerate (step 570). The final composition as disclosed herein is now produced (step 575).

In an example, the following may be included in 300 ml of the disclosed composition: 195 ml of hydrolyzed soybeans with *Bacillus amyloliquefaciens* biomass (See FIG. 2), 15 ml of lactic bacteria solution (See FIG. 3), and 90 ml of *Auricularia polytricha*/Curcumin solution (See FIG. 4).

EXAMPLES

The disclosed composition shows effectiveness in the treatment of the diseases discussed herein. We observed no side effects in any study subject. The study subjects ranged from one to 80 years old and consuming the composition for a long period of time—ranging from one week to multiple months. The benefits composition improved according to our studies include the following:

First Benefit: Detoxify the body, improve digestive system, boost immune system: inflammatory bowel disease (IBS), chronic hepatitis, gastritis (ulcer, inflammation, *Helicobacter pylori*), hemorrhoids, and colorectal polyps.

Second Benefit: Treat or prevent diseases due to lipid disorders including coronary heart disease, atherosclerosis, and hyperlipidemia.

Third Benefit: Improve blood circulation to prevent or treat stroke, ischemia, platelet aggregation, sequel of strokes, and vertigo.

Subject demographics, the amount and frequency of the composition, and the results of the treatments are described below. All doses were consumed orally.

Study Number 1: First Benefit
Subject #1
Age/Gender: 64, Male
Main Disorders: liver and kidney cancer, chronic obstructive pulmonary disease (COPD), weak digestion—at times unable to digest food leading to fever
Doses: 50 ml of the composition given orally, 3 times per day between the years 2011-2019
Results: improved digestion. Subject #1 was often admitted to the intensive care unit (ICU) during the 2011-2019 period during which the subject suffered from liver and kidney cancers. He ingested exclusively formula milk and the disclosed composition. Subject #1 recovered quickly and was transferred out of ICU, usually after 24-48 hours. The disclosed composition seems to be an effective conduit to bring the active substances to the affected areas while boosting the immune system.
Subject #2
Age: 30
Main Disorders: acne, feeling hot, constipation, sleep disorder, and unnaturally thin
Dose: 100 ml or the composition given orally, 3 times per day (before meals)
Results: Subject #2 experienced no constipation after 3 days or treatment, reported feeling better after 5 days, became able to sleep at night, and acne lessened significantly.

Subject #3
Age/Gender: 62, Female
Main Disorders: high cholesterol, indigestion
Dose: 100 ml of the composition which included an increased amount of *Auricularia polytricha* given orally, 3 times per day
Results: Subject #3 experienced significantly healthier digestion after one week and lower cholesterol level after one month. Subject #3 continued daily doses of the composition.

Subject #4
Age: 64
Main Disorders: indigestion, constipation
Dose: 100 ml of the composition given orally, 3 times per day
Results: Subject #4 experienced significantly improved digestion after 3 days an no further constipation. Subject #4 continued to ingest the composition daily at reduced a dose of 100 ml per day.

Subject #5
Age/Gender: 40, Male
Main Disorders: indigestion, constipation
Dose: 100 ml of the composition given orally, 3 times per day
Results: Subject #5 experienced stable digestion after 3 days and continued to ingest 100 ml of the composition once or twice daily.

Subject #6
Age/Gender: 6, Male
Main Disorders: viral fever (elevated body temperature), coughing, nausea, fatigue, body aches)
Doses: 100 ml of the composition given orally, 3 times per day
Results: Subject #6 had no fever after 2 days.

Subject #7
Age/Gender: 83, Male
Main Disorders: colorectal polyp, bowel movement discomfort—painful and unstable
Doses: 100 ml of the composition given orally, 3 times per day
Results: Subject #7 experienced a significant improvement in ease of defecation with no further pain or other discomfort.

Subject #8
Age/Gender: 68, Female
Main Disorders: irritable bowel syndrome (IBS), indigestion, bowel movement discomfort
Doses: 100 ml of the composition, 3 times per day
Results: after 5 days, less abdominal discomfort, bowel movements induced, better digestion, feeling lightened Subject #9
Age: 60, Male
Main Disorders: cirrhosis with swollen abdomen (ascites) due to excessive alcohol consumption, indigestion, restless sleep, extreme discomfort during bowel movements requiring laxatives.
Doses: 150-200 ml of the composition given orally, 3 times per day Results: health conditions improved significantly after 3 days, better digestion, slept better; in combination with massage, acupuncture, biological transfer of energy and taking the disclosed composition together with a *Clinacanthus nutans* solution, health conditions improved remarkably after one month, able to move around easily, able to walk 300 meters, going up stairs without assistance.

Subject #10
Age/Gender: 33, Male
Main Disorders: stomach pain, diarrhea
Doses: 150 ml of the composition given orally at each dose
Results: Subject #10 had no more stomach pain within 10 minutes of the first dose. Subject #10 consumed two more doses of the composition, each separated by two hour times spans. Diarrhea ceased after the third dose.

Subject #11
Age/Gender: 55, Male
Main Disorders: hemorrhoid, bleeding at defecation
Doses: 50 ml of the composition per day, take orally before meals
Results: Subject #11 experienced improvement in her symptoms after 10 days of consuming the composition. Specifically, Subject #11 experienced less bleeding at defecation and the prolapsed hemorrhoid began getting smaller in size until it disappeared after 1.5 to 2 months. Subject #11 regained normal bowel movements.

Subject #12
Age/Gender: 32, Female
Main Disorders: hemorrhoids, bleeding at defecation
Doses: 50 ml per day, taken orally before meals
Results: Subject #12 stopped bleeding at defecation, experienced easier defecation events, burning pain in the anus ceased and the hemorrhoid disappeared after 2 months of continuously consuming the composition along with abstaining from food which Subject #12 experienced heat intolerance food.

Subject #13
Age/Gender: 15, Female
Main Disorders: indigestion, flatulence
Doses: 50 ml of the composition given orally at each dose
Results: Subject #13 experienced bowel movements 30 minutes after consuming the composition.

Subject #14
Age/Gender: 7, Female
Main Disorders: stomach pain, diarrhea
Doses: 50 ml of the composition per dose
Results: Subject #14 experienced no further stomach pain 15 minutes after consuming the first dose of the composition. Diarrhea ceased after the subject consumed two more doses of the composition. Each dose was spaced two hours apart.

Subject #15
Age/Gender: 33, Male
Main Disorders: hemorrhoids, burning pain at defecation
Doses: 50 ml of the composition per day taken orally before meals
Results: Subject #15 experienced less burning pain at defecation after a week of consuming the composition.

Study Number 2: Second Benefit

Subject #16
Age: 64, Male
Main Disorders: epilepsy, extremely high serum cholesterol, coronary artery stenosis for which 4 stents had been placed in coronary arteries (2 more stents were advised due to severe stenosis in branches of the main coronary artery, but they were unable to be placed due to the high level of difficulty and risk in performing the operation)
Doses: 100 ml of the composition given orally, 3 times per day
Results: Subject #16 experienced no angina after 3 months of consuming the composition and had no further convulsive seizures.

Subject #17
Age/Gender: 62, Female
Main Disorders: elevated serum cholesterol, indigestion
Dose: 100 ml of the composition given orally which included an increased amount of *Auricularia polytricha*, 3 times per day
Results: Subject #17 experienced significantly healthier digestion after one week and reduced serum cholesterol level after one month. Subject #17, continues the dosing regimen daily.
Study Number 3: Third Benefit
Subject #18
Age/Gender: 33, Female
Main Disorders: severe bruising to upper arm caused by physical trauma (Subject #18 experienced a fall)
Dose: 200 ml of the composition per day given orally
Results: Subject #18 had no more bruising after five days.
Subject #19
Age/Gender: 33, Male
Main Disorders: finger laceration which was sutured then became infected accompanied by severe swelling and sensory loss; took pills for a week with no results.
Doses: 400 ml of the composition per day given orally
Results: After 7 days, the swelling in the finger diminished considerably.
Subject #20
Age/Gender: 62, Male
Main Disorders: stroke followed by groggy feeling
Doses: 200 ml of the composition per day given orally
Results: Subject #20 ceased feeling groggy.
Subject #21
Age/Gender: 68, Male
Main Disorders: occasionally experienced quick lancing pains when urinated, dizziness when turned head around quickly
Doses: 50-100 ml of the composition given orally 3 times per day with continued use
Results: Subject #21 has experienced no pain when urinating for 6 years now, ceased to be dizzy when turning his head quickly; experienced stable health conditions, normal digestion, normal sweating & urination; lightened body state, and improved bowel movements.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method of treating a gastrointestinal disease by administering a composition to a subject in need thereof, the composition comprising:
   a. soybean;
   b. *Bacillus amyloliquefaciens*;
   c. a plurality of strains of lactic acid bacteria wherein the lactic acid bacteria are produced from a sterilized soybean solution;
   d. *Auricularia polytricha*; and
   e. *Curcuma longa* (turmeric),
   wherein the composition is prepared by:
   hydrolyzing a mixture of a culture of the *Bacillus amyloliquefaciens* and the soybean in a ratio of approximately 5% by volume, wherein the soybean is ground, boiled, and cooled to a room temperature of approximately 28 to 32 degrees Celsius;
   adding the lactic acid bacteria to the hydrolyzed mixture in a ratio of 5%;
   adding the *Auricularia polytricha* and the *Curcuma longa* to the hydrolyzed mixture that includes the lactic acid bacteria, wherein the *Auricularia polytricha* measures 100 grams in weight, and the *Curcuma longa* measures 100 grams in weight to obtain the composition; and
   refrigerating the composition prior to the administering.

2. The method of claim 1, wherein the gastrointestinal disease comprises gastric *Helicobacter pylori* infection.

3. The method of claim 1, wherein the *Bacillus amyloliquefaciens* is a combination of endospores and vegetative cells.

4. The method of claim 1, wherein the plurality of strains of lactic bacteria comprise at least one of *Lactobacillus bulgaricus, Streptococcus thermophilus*, and *Lactobacillus casei*.

5. The method of claim 1, wherein the plurality of strains of lactic acid bacteria comprise *Lactobacillus bulgaricus, Streptococcus thermophilus*, and *Lactobacillus casei*.

6. The method of claim 1, wherein the plurality of strains of lactic acid bacteria consist of *Lactobacillus bulgaricus, Streptococcus thermophilus*, and *Lactobacillus casei*.

7. The method of claim 1, wherein the soybean comprises whole soybeans.

8. The method of claim 1, wherein the soybean is fermented.

9. The method of claim 8, wherein the soybean is fermented by the *Bacillus amyloliquefaciens*.

10. The method of claim 1, wherein the composition is administered orally at least once per day.

11. The method of claim 1, wherein the composition is administered orally three times per day.

12. The method of claim 1, wherein the composition is administered orally before a meal.

13. The method of claim 1, wherein the composition is administered three times per day, orally, and before a meal.

14. The method of claim 1, wherein the composition is administered in a volume between 50 ml and 300 ml.

15. The method of claim 1, wherein the composition is administered at least once per day in a volume between 50 ml and 300 ml per dose.

16. The method of claim 1, wherein the composition is administered three times per day in a volume between 50 ml and 100 ml per dose.

17. The method of claim 1, wherein the subject is a human.

18. The method of claim 1, wherein the composition is provided as either a solution, a dried powder, a tablet, or a capsule.

19. A method of treating a gastrointestinal disease by administering a composition to a subject in need thereof, the composition comprising:
   a. seeds or fruit;
   b. *Bacillus amyloliquefaciens;*
   c. a plurality of strains of lactic acid bacteria;
   d. *Auricularia polytricha*; and
   e. *Curcuma longa* (turmeric),
   wherein the composition is prepared by:
   fermenting the seeds or fruit by the *Bacillus amyloliquefaciens;*
   adding the lactic acid bacteria to the fermented mixture in a ratio of 5%;
   adding the *Auricularia polytricha* and the *Curcuma longa* to the fermented mixture that includes the lactic acid bacteria, wherein the *Auricularia polytricha* measures 100 grams in weight, and the *Curcuma longa* measures 100 grams in weight to obtain the composition; and
   refrigerating the composition prior to final use.

20. The method of claim 19, wherein the seeds or fruit comprises avocado.

* * * * *